United States Patent
Kreutzer

(10) Patent No.: US 9,482,582 B2
(45) Date of Patent: Nov. 1, 2016

(54) INSPECTION SYSTEM WITH TEMPERATURE MEASUREMENT DEVICE

(71) Applicant: iPEK International GmbH, Sulzberg (DE)

(72) Inventor: Alexander Kreutzer, Sonthofen (DE)

(73) Assignee: iPEK International GmbH, Sulzberg (DE)

( * ) Notice: Subject to any disclaimer, the term of this patent is extended or adjusted under 35 U.S.C. 154(b) by 404 days.

(21) Appl. No.: 14/024,231

(22) Filed: Sep. 11, 2013

(65) Prior Publication Data

US 2014/0072012 A1 Mar. 13, 2014

(30) Foreign Application Priority Data

Sep. 11, 2012 (DE) .................. 10 2012 108 500

(51) Int. Cl.

| | |
|---|---|
| *G01J 5/00* | (2006.01) |
| *G01K 1/08* | (2006.01) |
| *G01K 13/00* | (2006.01) |
| *G01J 5/04* | (2006.01) |
| *G01N 25/72* | (2006.01) |
| *E03F 7/12* | (2006.01) |
| *G01N 21/954* | (2006.01) |

(52) U.S. Cl.
CPC .................. *G01J 5/04* (2013.01); *G01J 5/043* (2013.01); *G01J 5/047* (2013.01); *G01N 25/72* (2013.01); *E03F 7/12* (2013.01); *G01N 2021/9542* (2013.01)

(58) Field of Classification Search
USPC ................. 374/121, 148, 208, 143
See application file for complete search history.

(56) References Cited

U.S. PATENT DOCUMENTS

| | | | | |
|---|---|---|---|---|
| 3,483,734 | A * | 12/1969 | Wood .................... | G01M 3/002 374/4 |
| 3,761,713 | A * | 9/1973 | Merrill ................... | G01V 9/005 374/124 |
| 3,885,091 | A * | 5/1975 | Fish ........................ | G01M 3/38 348/164 |
| 4,651,558 | A * | 3/1987 | Martin ..................... | E03F 7/12 348/84 |
| 4,855,838 | A * | 8/1989 | Jones .................... | H04N 5/2251 348/345 |
| RE33,160 | E * | 2/1990 | Guthrie .................... | E03F 7/12 348/84 |
| 4,913,558 | A * | 4/1990 | Wettervik ............... | G01M 3/38 348/164 |
| 5,158,365 | A * | 10/1992 | Kreuz .................... | C22C 27/04 136/236.1 |

(Continued)

FOREIGN PATENT DOCUMENTS

| | | |
|---|---|---|
| DE | 20 2004 013 240 U1 | 12/2004 |
| DE | 601 32 590 T2 | 1/2009 |

OTHER PUBLICATIONS

English translation of the German Search Report issued for corresponding German Patent Application No. 10 2012 108 500.5 mailed on May 15, 2013.

*Primary Examiner* — Mirellys Jagan
(74) *Attorney, Agent, or Firm* — Myers Wolin, LLC

(57) ABSTRACT

An inspection system, in particular, a sewer inspection system is provided, comprising a temperature measurement device, whereby the temperature measurement device is a pyrometer for contact-free measurement of a surface temperature of an object, in particular, a pipe wall. Advantageously, the pyrometer is configured as an infra-red temperature sensor.

6 Claims, 2 Drawing Sheets

(56) References Cited

U.S. PATENT DOCUMENTS

| | | | | |
|---|---|---|---|---|
| 5,195,392 A * | 3/1993 | Moore | | F16L 55/18 |
| | | | | 138/97 |
| 6,271,878 B1 * | 8/2001 | Sera | | G01N 25/72 |
| | | | | 348/164 |
| 6,545,704 B1 * | 4/2003 | Olsson | | H04N 7/183 |
| | | | | 348/84 |
| 8,864,372 B2 * | 10/2014 | Buisson | | G01K 13/00 |
| | | | | 374/141 |
| 2002/0012049 A1 * | 1/2002 | Woodstock | | H04N 5/2252 |
| | | | | 348/207.99 |
| 2003/0198374 A1 * | 10/2003 | Hagene | | G01N 21/954 |
| | | | | 382/141 |
| 2005/0005716 A1 * | 1/2005 | Harris | | G01M 3/18 |
| | | | | 73/865.8 |
| 2005/0089076 A1 * | 4/2005 | Lindstrom | | H04N 5/33 |
| | | | | 374/16 |
| 2005/0115338 A1 * | 6/2005 | McGrew | | E03F 3/06 |
| | | | | 73/865.8 |
| 2006/0153275 A1 * | 7/2006 | Ishikawa | | G01J 5/0022 |
| | | | | 374/141 |
| 2009/0255332 A1 * | 10/2009 | Bunker | | G01F 1/68 |
| | | | | 73/204.11 |
| 2011/0310240 A1 * | 12/2011 | Sudano | | H04N 7/185 |
| | | | | 348/84 |
| 2012/0222993 A1 * | 9/2012 | Biesse | | E03F 7/12 |
| | | | | 210/85 |
| 2012/0257042 A1 * | 10/2012 | McKaigue | | G01N 21/954 |
| | | | | 348/84 |
| 2015/0063410 A1 * | 3/2015 | Kajiyama | | G02B 26/10 |
| | | | | 374/57 |
| 2015/0185392 A1 * | 7/2015 | Cai | | G02B 6/0038 |
| | | | | 362/606 |
| 2015/0334781 A1 * | 11/2015 | Verhagen | | H05B 6/101 |
| | | | | 219/667 |

* cited by examiner

INSPECTION SYSTEM WITH TEMPERATURE MEASUREMENT DEVICE

CROSS-REFERENCE TO RELATED APPLICATIONS

This application claims priority to German Application No. 10 2012 108 500.5, filed on Sep. 11, 2012, the contents of which are hereby incorporated by reference.

FIELD OF THE INVENTION

The invention relates to an inspection system, in particular, a sewer inspection system with a temperature measurement device.

BACKGROUND OF THE INVENTION AND PRIOR ART

For inspection of conduits, in particular, sewer conduits, pits, connecting conduits, property drainage systems, seepage water lines or other waste water related plants it may be necessary to also detect and evaluate the temperature in the interior of a conduit or the temperature profile along the conduit besides the visual inspection of the conduits which may be carried out by means of TV sewer inspection systems.

For detection of the temperature in the interior of the conduit to be inspected, inspection systems or sewer inspection systems, respectively, are known which comprise temperature measurement devices. By means of these temperature measurement devices, however, only the temperature of the atmosphere in the interior of the conduit can be measured. Such a measurement, however, is considered to be inaccurate, because disturbances, as for example, a high air flow or air circulation, respectively, in the interior of the conduit can distort the results of the measurement and, in the worst case, render them useless. A further disturbance which may affect or distort, respectively, the measurement of the temperature is the system temperature of the inspection system which with increasing time of use increases continuously, and thus, may also raise the ambient temperature. Air flow or air circulations, respectively, in the conduit to be inspected may, in particular, substantially affect the detection of a temperature curve or the generation of a temperature profile or, in the worst case, even make it impossible.

OBJECT

Therefore, the present invention is based on the object to at least partially avoid the disadvantages known from prior art and to provide an inspection system by means of which an accurate measurement and, in particular, free of any disturbances of a temperature in the interior of a conduit is enabled.

SUMMARY

According to the invention, this object is solved by an inspection system, in particular, by a sewer inspection system with a temperature measurement device according to the independent claim. Preferred embodiments of the invention are defined in the dependent claims.

Thus, an inspection system, in particular, a sewer inspection system is provided comprising a temperature measurement device whereby the temperature measurement device is a pyrometer for contact-free measurement of a surface temperature of an object, in particular, a conduit wall.

The inspection system may be a self propelled inspection system, i. e., with an own drive, or may be a slidable inspection system which has an own drive, and which is pushed via a strong cable or linkage into the sewer pipe.

The contact free measurement of the surface temperature of the conduit wall has the advantage that no longer the ambient temperature within the sewer pipe to be inspected has to be measured such that the measurement of the temperature may be carried out independently of disturbances, in particular, air flows or air turbulences, respectively, within the sewer pipe which avoids a distortion of the measurement results to a large extent. Further, thereby it is avoided that the system temperature of the inspection system influences the temperature measurement.

The pyrometer may comprise an infra-red temperature sensor. The inspection system according to the invention may comprise an inspection carriage whereby the temperature measurement device and the infra-red temperature sensor, respectively, are arranged at the inspection carriage.

In a preferred embodiment of the invention, the temperature measurement device may be arranged pivotably around a longitudinal axis of the inspection carriage at the inspection carriage. Thereby, the temperature may be measured advantageously at various locations of the inner wall of the sewer pipe to be inspected such that different temperature profiles for one sewer pipe may also be generated.

In a preferred embodiment of the invention, the temperature measurement device also comprises a housing whereby the pyrometer and the infra-red temperature sensor, respectively, may be arranged within the interior of the housing, and whereby a section of the housing is configured to be at least partially translucent, in particular, translucent to infra-red light. Thereby, the pyrometer and the infra-red temperature sensor, respectively, may be protected against external influences, for example, spray water or dirt.

The section of the housing which is configured to be at least partially translucent or translucent to infra-red light, may comprise glass, quartz glass, germanium, calcium fluoride, zinc sulfide, zinc selenide, thallium bromide iodide, polyethylene, polypropylene, or a combination thereof.

It is advantageous, if the housing is configured to be pressure-tight. It is especially preferred, if the housing is filled with a non-inflammable gas, in particular, nitrogen, whereby the pressure in the interior of the housing is higher than the ambient pressure. In the interior of the housing, a pressure sensor may be arranged.

Further, it is advantageous, if the housing is configured to be water-tight such that a temperature measurement can also be carried out, if the housing is partially or completely within water.

According to an embodiment of the invention, the temperature measurement device and the housing with the pyrometer, respectively, or the infra-red temperature sensor, respectively, may be arranged at a camera head of the inspection system. Hereby, it is preferred, if the camera head is arranged rotatably around its longitudinal axis or pivotably at the inspection system, respectively. Thereby, a temperature measurement can be advantageously carried out in the area of the inner wall of a sewer pipe which substantially lies within the field of vision of the camera.

BRIEF DESCRIPTION OF THE FIGURES

Further details and features of the invention as well as concrete, in particular, preferred embodiments of the invention may be taken from the following description in connection with the drawing.

DETAILED DESCRIPTION OF THE INVENTION

Figure 1:
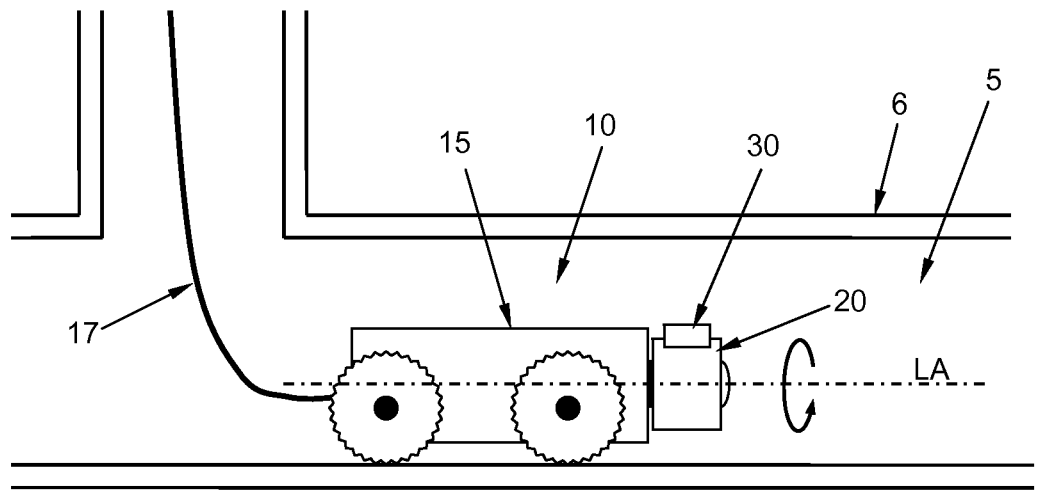
FIG. 1 shows a diagrammatic illustration of an inspection system with a temperature measurement device arranged thereon within a sewer pipe.

FIG. 1 shows an inspection system or a sewer inspection system 10, respectively, according to the invention, which is located within a pipe or conduit 5, respectively, to be inspected.

The inspection system 10 comprises an inspection carriage 15 which here is configured as camera carriage. To the rear side of the inspection carriage 15, a power and/or data cable 17 is connected which is guided to the outside to a measurement carriage or to an operator not shown here. Via the power or data cable 17, respectively, the inspection carriage 15 and the electronic assembly group and components, respectively, can be supplied with energy and control data as well as the measurement data generated during the inspection may be transmitted to the outside to operators.

An image capturing device is arranged at the front end of the inspection carriage or the camera carriage 15, respectively, which here is configured as a camera head 20. The camera head 20 comprises in the embodiment shown here a CCD sensor (CCD camera) or a CMOS sensor (CMOS camera), respectively. However, also other digital imaging sensors may be used. In the embodiment of an inspection system 10 according to the invention shown here, the camera head 20 is configured to be rotatable around its longitudinal axis LA. Additionally, the camera head 20 may be hinged to the camera carriage 15 via a pivoting device not shown here in order to pivot the camera head 20 in a horizontal and/or vertical direction and to tilt it about a predetermined angle to the front or backwards, respectively.

A temperature measurement device 30 is provided at the inspection carriage 15 which is arranged at the camera head 20 in the embodiment of an inspection system according to the invention shown in FIG. 1. Thereby, the temperature measurement device 30 may be rotated together with the camera head 20 around the longitudinal axis LA of the camera head and/or may be pivoted together with the camera head, respectively, or may be tilted together with the camera head to the front or backwards, respectively.

According to the invention, the temperature measurement device 30 comprises a pyrometer for contact-free measurement of the surface temperature of an object, for example, a conduit wall 6. In a preferred embodiment of the invention, the pyrometer comprises an infra-red temperature sensor which is arranged in a housing of the temperature measurement device 30 which will be further explained with reference to FIG. 2.

By means of the pyrometer or the infra-red temperature sensor, respectively, heat radiation emitted from the conduit inner wall 6 or emitted from the depositions or incrustations on the conduit inner wall, respectively, may be detected, the intensity of which depends on the temperature of the conduit wall and on the temperature of the depositions, respectively. The essential advantage of a pyrometer or of an infra-red temperature sensor, respectively, and their use in an inspection system, in particular, in a sewer inspection system, respectively, is that the temperature of the pipe wall 6 and the depositions, respectively, may be measured independently of the system temperature of the inspection system and independently of the atmosphere temperature in the conduit 5. It is especially preferred that disturbances, for example, air flow or air circulations in the sewer pipe only have a negligibly small influence on the measurement and on the measurement results, respectively.

As detectors for the pyrometer, thermal detectors may be provided, for example bolometers or pyroelectrical sensors. However, photoelectric sensors have been found to be advantageous, for example, non-cooled or cooled photo diodes. The contact-free temperature measurement additionally has the advantage that a very fast measurement between 10 µs and 1 s is possible such that the generation of a heat profile for a pipe is realizable in a relatively short time. A further advantage is that at least the used detectors are subject to almost no wear.

The measurement values taken by the temperature measurement device 30 can be transmitted via the data cable 17 to the outside to operators where they may be evaluated and/or further processed.

Figure 2:
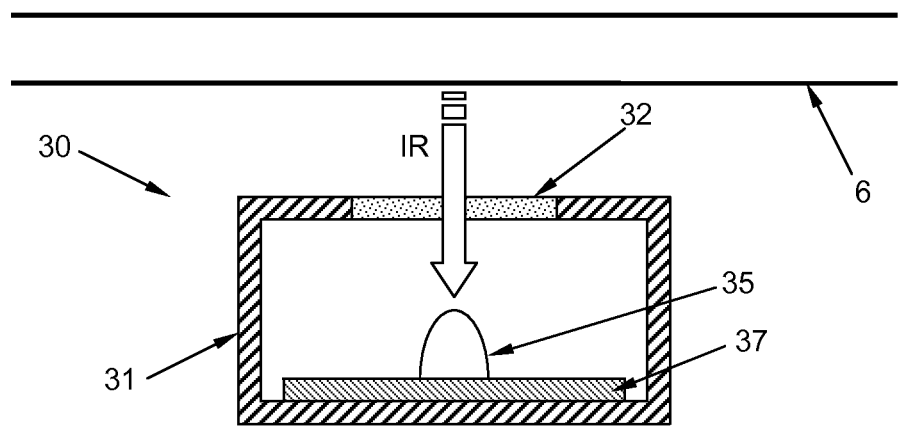
FIG. 2 shows a section through the housing of a temperature measurement device according to the invention.

FIG. 2 shows a temperature measurement device 30 according to the invention in a sectional view.

The temperature measurement device 30 consists of a housing 31 in which an infra-red temperature sensor 35 is arranged. The infra-red temperature sensor 35 may be arranged on a circuit board 37 on which further electrical components for the operation of the infra-red temperature sensor 35 may be arranged. Not shown in FIG. 2 are the data and power cables, respectively, which are guided out of the housing 31 which may be coupled to a data processing unit and/or to a control unit of the inspection carriage 15. Alternatively, the data and power cables, respectively, guided out of the housing 31 may also be guided to the outside to the operators via the power and/or data cable 17.

Preferably, the housing 31 of the temperature measurement device 30 is made from a strong material, for example, metal or from a dimensionally stable plastic material. At least in a portion 32, the housing is configured to be translucent or translucent to infra-red light, respectively, such that the infra-red radiation IR emitted from the conduit inner wall 6 may reach the infra-red temperature sensor 35 in the interior of the housing 31. It has been found to be advantageous, if the translucent area or the area 32 translucent to infra-red light, respectively, of the housing 31 comprises glass, quartz glass, germanium, calcium fluoride, zinc sulfide, zinc selenide, thallium bromide iodide, polyethylene, or polypropylene. A translucent area or translucent area to infra-red light 32, respectively, from germanium has been found to be especially advantageous. Further, it may be advantageous to configure the translucent area or the area translucent to infra-red light 22, respectively, lens-shaped.

The temperature measurement device 30 and the housing 31, respectively, shown in FIG. 2 is configured to be pressure- and water-tight such that the temperature measurement device according to the invention may also be used in a wet environment, for example, in a water-bearing pipe. It is advantageous, if an overpressure compared to the ambient pressure prevails in the housing 31 such that a pressure loss may be detected by means of a pressure sensor arranged in the interior of the housing 31. For generation of an overpressure, the housing 31 may be filled with a non-inflammable material, for example, nitrogen, which is advantageous especially when the inspection system is used in potentially explosive environments.

Figure 3:
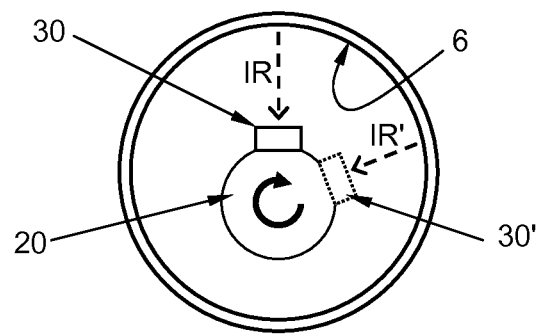
FIG. 3 shows a cross-section through a camera head with a temperature measurement device arranged thereon at different rotation angles of the camera head.

FIG. 3 shows the camera head 20 shown in FIG. 1 in a front view and at two different rotation angles.

The temperature measurement device 30 according to the invention is arranged at the camera head 20 such that in a resting position of the camera head 20, i.e., at a rotation angle of approximately 0°, infra-red radiation IR which is emitted from the upper inner wall 6 of the pipe at which the infra-red temperature sensor is arranged, may reach the infra-red temperature sensor which is arranged in the interior of the housing. In this position of the camera head, a first temperature profile of the pipe may be generated.

By rotation of the camera head 20 around its longitudinal axis LA, the temperature measurement device 30 arranged also at the camera head 20 is pivoted about the longitudinal axis of the camera head. The temperature measurement device pivoted about a certain angle is shown in FIG. 3 as temperature measurement device 30'. In this position, the temperature of the lateral inner wall 6 of the pipe may be measured in that the infra-red radiation IR' emitted from the lateral inner wall is able to reach the infra-red temperature sensor of the temperature measurement device 30'. In this position of the camera head, a second temperature profile of the pipe may be generated. Thereby, it is enabled to generate different temperature profiles of a pipe. With rotation of the camera head 20 of about 180° such that the temperature measurement device is directed downwards, also a temperature profile of the bottom of the pipe may be generated.

The temperature measurement device 30 in the embodiment of an inspection system according to the invention shown here is arranged at the camera head 20 to be able to be pivoted together with the camera head 20 and/or tilted. Of course, the temperature measurement device 30 may also be arranged at another position of the inspection carriage. For example, the temperature measurement device 30 may be arranged fixedly on the surface of the inspection carriage 15, if only temperature measurements in the upper region, i.e., at the ceiling of the pipe, are to be carried out. Alternatively, the temperature measurement device 30 may also be arranged at a further pivot device which may be pivoted and/or tilted independently of the camera head.

Figure 4:
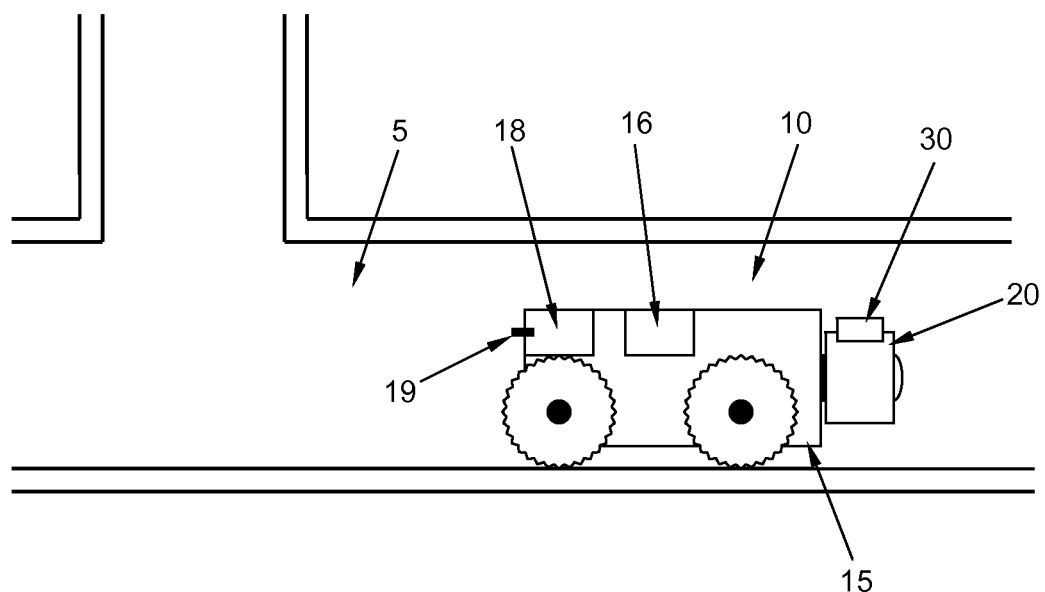
FIG. 4 shows a further embodiment of the inspection system according to the invention.

FIG. 4 shows a schematic illustration of an inspection system 10 according to the invention in an alternative configuration.

The inspection system 10 generally corresponds to the inspection system 10 shown in FIG. 1 and has an inspection carriage 15 at the front end of which a camera head 20 is arranged. Further, a temperature measurement device 20 according to the invention is arranged at the camera head 20. Different from the inspection system 10 shown in FIG. 1, the inspection carriage 15 is not connected to a control unit arranged outside of the sewer system via a power or data cable 17, respectively.

Instead of a power or data cable, respectively, the inspection carriage 15 has a transmitting-/reception unit 18 for wireless data transmission. For this, the transmitting-/reception unit 18 has a transmitting-/receiving antenna 19. By means of the transmitting-/reception unit 18, measurement data may be transmitted to the control unit outside the pipe or control data may be received from the control unit in a wireless manner. The measurement data transmitted may comprise measurement data of the temperature measurement device 30. The control data may comprise control data by means of which the temperature measurement device 30 and/or the camera head 20 may be controlled. In an embodiment of the invention, the transmitting-/reception unit 18 may be configured as WLAN transmitter or WLAN receiver, respectively.

Further, the inspection carriage 15 shown in FIG. 4 comprises a storage means and/or data processing means 16. Measurement values, for example, measurement values of the temperature measurement device 30 may be pre-processed and stored by means of the storage means and/or data processing means such that a data transmission via the transmitting unit 18 may be dispensed with.

In the embodiment shown in FIG. 4 of the inspection system according to the invention without power or data cable 17, respectively, it is provided to supply the inspection carriage 15 and the components arranged on the inspection carriage 15, respectively, with power by a battery or an accumulator. In particular, also the temperature measurement device 30 according to the invention and the infra-red temperature sensor 35, respectively, may be supplied with the required energy by means of the battery or by means of the accumulator, respectively.

It is advantageous, if the inspection system and, in particular, also the temperature measurement device 30 are configured such that they also can be used in explosion-prone areas such that also there, temperatures and temperature profiles, respectively, may be taken.

REFERENCE NUMERALS 5 pipe, for example, sewer pipe
6 pipe wall or inner wall, respectively, of the sewer pipe
10 inspection system, in particular, sewer inspection system
15 inspection carriage, for example, camera carriage
16 storage means and/or data processing means
17 power and/or data cable
18 transmitting-/reception unit for wireless data transmission
19 transmitting-/receiving antenna of the transmitting-/reception unit
20 camera head
30, 30' temperature measurement device
31 housing of the temperature measurement device
32 translucent or infra-red translucent portion of the housing
35 infra-red temperature sensor (IR detector)
37 circuit board
IR, IR' infra-red radiation
LA longitudinal axis of the inspection system and the camera head, respectively

The invention claimed is:

1. An inspection system for inspecting a sewer comprising a temperature measurement device, wherein the temperature measurement device contains,
   a pyrometer for contact-free measurement of a surface temperature of an object,
   wherein the pyrometer comprises an infra-red temperature sensor,
   wherein the temperature measurement device comprises a housing,
     whereby the infra-red temperature sensor is arranged in an interior of the housing,
     whereby at least a portion of the housing is configured to be at least partially translucent to infra-red light,
   wherein the housing is configured to be pressure tight, and
   wherein the housing is filled with nitrogen, whereby the pressure in the interior of the housing is higher than an ambient pressure, and whereby a pressure sensor is arranged in the interior of the housing.

2. The inspection system of claim 1, wherein the portion of the housing configured to be at least partially translucent comprises at least one of glass, quartz glass, germanium, calcium fluoride, zinc sulfide, zinc selenide, thallium bromide iodide, polyethylene, and polypropylene.

3. The inspection system of claim 1, wherein the housing is configured to be water-tight.

4. The inspection system of claim 1, wherein the temperature measurement device is arranged at a camera head of the inspection system.

5. The inspection system of claim 1, further comprising an inspection carriage, wherein the temperature measurement device is arranged at the inspection carriage.

6. The inspection system of claim 5, wherein the temperature measurement device is arranged pivotably around a longitudinal axis of the inspection carriage at the inspection carriage.

* * * * *